United States Patent
Wong

(10) Patent No.: US 6,344,580 B1
(45) Date of Patent: Feb. 5, 2002

(54) PROCESS FOR THE PREPARATION OF 2,2-DIMETHYL-5-(4-CHLOROBENZYL) CYCLOPENTANONE AND AN INTERMEDIATE USEFUL THEREFORE

(75) Inventor: George S. K. Wong, Summit, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/878,000

(22) Filed: Jun. 8, 2001

Related U.S. Application Data

(60) Provisional application No. 60/210,768, filed on Jun. 12, 2000.

(51) Int. Cl.⁷ .............................................. C07C 255/46
(52) U.S. Cl. ...................................................... 558/405
(58) Field of Search ......................................... 558/405

(56) References Cited

U.S. PATENT DOCUMENTS

| | | | | |
|---|---|---|---|---|
| 4,938,792 A | | 7/1990 | Kumazawa et al. ............ | 71/92 |
| 5,028,254 A | | 7/1991 | Kumazawa et al. ............ | 71/92 |
| 5,414,105 A | * | 5/1995 | Kumazawa et al. .......... | 560/51 |
| 5,681,979 A | * | 10/1997 | Hoshi et al. .................. | 560/51 |

FOREIGN PATENT DOCUMENTS

| | | | | |
|---|---|---|---|---|
| EP | 0655443 | * | 5/1995 | |
| EP | 0731083 A1 | | 9/1996 | ......... C07C/69/757 |
| EP | 0731083 | * | 9/1996 | |

OTHER PUBLICATIONS

Kulp et al. Synthesis of 2,2–Disubstituted–5–Cyanocyclopentanones, Canadian Journal of Chemistry, 1965 43), pp. 2512–2515.

Romanelli et al, "A Search For Calcium–Channel Activators In the Verapamil Series", Il Farmaco, 1989, (44) pp. 449–464.

Herron et al., Leukotriene $B_4$ Receptor Antagonists: The LY255283 Series of Hydroxyacetophenones, Journal of Medicinal Chemistry, 1992, (35) 1818–1828.

* cited by examiner

Primary Examiner—Floyd D. Higel
Assistant Examiner—Golam M. M Shameem
(74) Attorney, Agent, or Firm—Charles F. Costello

(57) ABSTRACT

There is provided a process for the prepartion of 2,2-dimethyl-5-(4-chlorobenzyl)cyclopentanone.

(I)

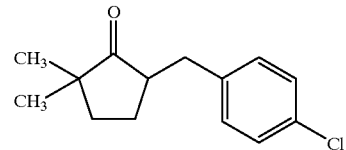

a key intermediate in the production of the antifungal agent metconazole.

Also provided is the intermediate compound, 5-(4-chlorobenzyl)-5-cyano-2,2-dimethylcyclopentanone (II)

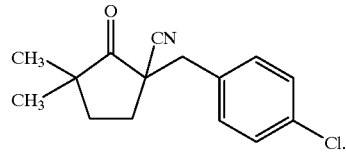

14 Claims, No Drawings

PROCESS FOR THE PREPARATION OF 2,2-DIMETHYL-5-(4-CHLOROBENZYL) CYCLOPENTANONE AND AN INTERMEDIATE USEFUL THEREFORE

This application claims the benefit under 35 U.S.C. 119(e) of provisional application 60/210,768 filed Jun. 12, 2000.

BACKGROUND OF THE INVENTION

A process for the preparation 2,2-dimethyl-5-(4-chlorobenzyl)-cyclopentanone, a key intermediate in the production of the anti-fungal agent metconazole is described in U.S. Pat. No. 5,028,254 and U.S. Pat. No. 4,938,792. Metconazole is highly effective for the control of a wide range of foliar diseases caused by phytopathogenic fungi which damage a number of important agronomic crops. Alternative, effective methods for the preparation of metconazole contribute to the enhanced availability of this useful fungicidal agent. Although, methods such as those mentioned hereinabove are known, said methods require extreme low temperature conditions for the prepartion of the intermediate 2,2-dimethyl-5-(4-chlorobenzyl) cyclopenanone.

Therefore, the preparation of 2,2-dimethyl-5-(4-chlorobenzyl)cyclopentanone continues to be studied for new and improved procedures which are more efficient and environmentally benign.

It is an object of the present invention to provide an improved process for the preparation of 2,2-dimethyl-5-(4-chlorobenzyl)cyclopentanone.

It is a further object of the invention to provide a compound, 5-(4-chlorobenzyl)-5-cyano-2,2-dimethylcyclopentanone, useful in an improved manufacture of metconazole.

SUMMARY OF THE INVENTION

There is provided a process for the preparation of 2,2-dimethyl-5-(4-chlorobenzyl)cyclopentanone (I)

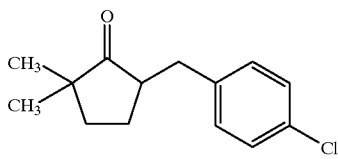

(I)

which comprises the following steps:
(a) reacting isobutyronitrile with 1-bromo-3-chloropropane in the presence of a first base in a non-polar solvent at a temperature of about 15° to 65°C. to afford 5-chloro-2,2-dimethylpentanenitrile;
(b) treating said 5-chloro-2,2-dimethylpentanenitrile with a cyanide-delivering reagent in the presence of a phase-transfer catalyst to form 2,2-dimethyladiponitrile;
(c) cyclizing said 2,2-dimethyladiponitrile in the presence of a second base in a non-polar solvent to afford 3,3-dimethyl-2-amino-1-cyanocyclopentene;

(d) hydrolyzing said 3,3-dimethyl-2-amino-1-cyanocyclopentene; in the presence of an acid to give 5-cyano-2,2-dimethylcyclopentanone;
(e) treating said 5-cyano-2,2-dimethylcyclopentanone with 4-chlorobenzyl chloride in the presence of a third base in a polar aprotic solvent to form 5-(4-chlorobenzyl)-5-cyano-2,2-dimethylcyclopentanone; and
(f) hydrolyzing said 5-(4-chlorobenzyl)-5-cyano-2,2-dimethylcyclopentanone in the presence of an acid to give the desired compound 5-(4-chlorobenzyl)-2,2-dimethylcyclopentanone.

The invention further provides the compound, 5-(4-chlorobenzyl)-5-cyano-2,2-dimethylcyclopentanone.

DETAILED DESCRIPTION OF THE INVENTION

Previously described conditions for effecting the alkylation of isobutyronitrile with 1-bromo-3-chloropropane require the use of polar solvents and a reaction temperature of −78° C. (S. S. Kulp, V. B. Fish and N. R. Easton, *Can. J. Chem.*, 1965, 43,2512; M. N. Romanelli, F. Gaultiere, R. Mannhold and A. Chiarini, *Farmaco*, 1989, 44, 449). This temperature requirement is not readily attainable on a large manufacturing scale. Surprisingly, it has now been found that the alkylation of isobutyronitrile in a non-polar solvent, in the presence of a base such as lithium bis (trimethylsilylamide) or lithium dimethylamide proceeds in high yield when conducted at temperatures up to 65° C., thus permitting a more efficient and effective manufacturing procedure.

Advantageously, the present invention provides an effective and practical method for the preparation of 5-(4-chlorobenzyl)-2,2-dimethycyclopentanone, a key intermediate in the production of the antifungal agent metconazole.

In accordance with the process of the invention isobutyronitrile (III) is alkylated with at least one molar equivalent of 1-bromo-3-chloropropane in a non-polar solvent in the presence of a first base to yield 5-chloro-2,2-dimethylpentanenitrile (IV); said 5-chloro-2,2-dimethylpentanenitrile (IV) is treated with a cyanide-delivering reagent in the presence of a phase-transfer catalyst (Ptc) to yield 2,2-dimethyladiponitrile (V); said 2,2-dimethyladiponitrile (V) is cyclized in the presence of a second base in a non-polar solvent to form 3,3-dimethyl-2-amino-1-cyanocyclopentene. Advantageously, the thus-formed 3,3-dimethyl-2-amino-1-cyanocyclopentene (VI) may be carried on without isolation or purification to acid hydrolysis to form 5-cyano-2,2-dimethylcyclopentanone (VII). Said cyclopentanone (VII) is then alkylated with 4-chlorobenzyl chloride in the presence of a third base in a polar aprotic solvent to give the intermediate 5-(4-chlorobenzyl)-5-cyano-2,2-dimethylcyclopentanone (II). Finally, said pentanone is hydrolyzed with acid to provide 5-(4-chlorobenzyl)-2,2-dimethylcyclopentanone (I). The process is depicted in Flow Diagram I.

FLOW DIAGRAM I

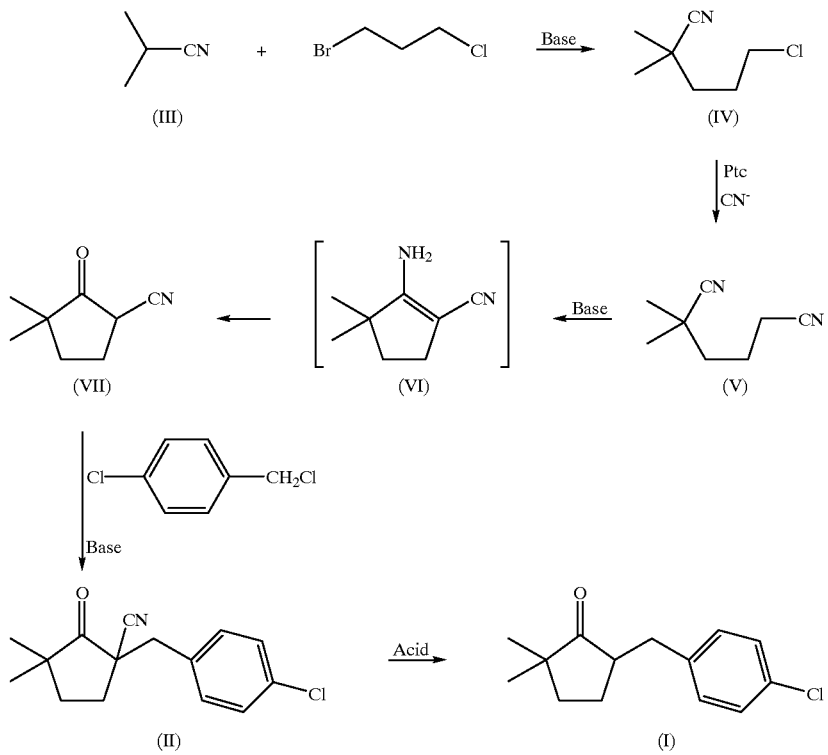

Non-polar solvents suitable for use in the process of the invention are essentially water-free solvents such as aromatic hydrocarbons (e.g. toluene, benzene, xylene, naphthalene or the like, preferably toluene), halogenated aromatic hydrocarbons (e.g. chlorobenzene, dichlorobenzene or the like), hydrocarbons (e.g. pentane, hexane or the like), halogenated hydrocarbons (e.g. chloroform, methylene chloride, dichlorethane, or the like, or any of the conventional, preferably water immiscible, organic non-polar solvents.

Preferred non-polar solvents suitable for use in the process of the invention are hydrocarbons and aromatic hydrocarbons such as hexane, heptane, toluene, ethylbenzene or the like.

Polar aprotic solvents suitable for use in the inventive process are dimethyl formamide, dimethylsulfoxide, tetrahydrofuran, diethyl ether, or the like.

Preferred polar aprotic solvents suitable for use in the process of the invention are dimethylformamide and dimethylsulfoxide.

Bases suitable for use as the first base in the inventive process are alkali metal amides, such as lithium amide, lithium dimethylamide, sodium bis(trimethylsilyl)amide, magnesiochlorodiethylamide (Et$_2$NMgCl), preferably lithium bis(trimethylsilyl)amide or lithium amide.

Bases suitable for use as the second base in the inventive process are alkali metal alkoxides, such as sodium or potassium $C_1$–$C_4$ alkoxide, preferably sodium t-butoxide.

Bases suitable for use as the third base in the inventive process are alkali metal hydrides, such as sodium, potassium or lithium hydride, preferably sodium hydride.

Bases may be present in amounts ranging from catalytic to excess amounts such as 10 mole % to 4.0 molar excess.

Acids suitable for use in the process of the invention include strong mineral acids such as HCl, HBr or H$_2$SO$_4$, preferably H$_2$SO$_4$.

The term catalysis refers to the enhancement of the rate of a reaction by the presence of a base when the base is left unchanged by the overall reaction. A phase transfer catalyst is a compound which facilitates the transfer of reactants across the interface of a two-phase organic-water system thereby enhancing the rate of reaction in said systems.

Phase-transfer catalysts suitable for use in the process of this invention are tetrabutylammonium hydrogen sulfate, tetrabutylammonium bromide, benzyltriethylammonium chloride, or the like, preferably tetrabutylammonium hydrogen sulfate.

In actual practice, isobutyronitrile (III) is alkylated with at least one molar equivalent of 1-bromo-3-chloropropane in a non-polar solvent, preferably a hydrocarbon, more preferably hexane, in the presence of a first base, preferably an alkali metal amide, more preferably lithium bis(trimethylsilylamide) or lithium dimethylamide, to yield 5-chloro-2,2-dimethylpentanenitrile (IV); said 5-chloro-2,2-dimethylpentanenitrile (IV) is treated with a cyanide-delivering reagent, preferably an alkali metal cyanide, more preferably sodium cyanide, in the presence of a phase-transfer catalyst, preferably tetrabutylammonium hydrogen sulfate, to yield 2,2-dimethyladiponitrile (V); said 2,2-dimethyladiponitrile (V) is cyclized in the presence of a second base, preferably an alkali metal alkoxide, more preferably sodium t-butoxide, in a non-polar solvent, preferably an aromatic hydrocarbon, more preferably toluene; the thus formed 3,3-dimethyl-2-amino-1-cyanocyclopentene (VI) advantageously may be carried on without isolation or purification to acid hydrolysis, preferably with a strong mineral acid, more preferably with sulfuric acid, to form 5-cyano-2,2-dimethylcyclopentanone (VII); said cyclopentanone (VII) is alkylated with 4-chlorobenzyl chloride in the presence of a third base, preferably an alkali metal hydride, more preferably sodium hydride, in a polar aprotic solvent, preferably N,N-dimethylformamide, to give the intermediate compound 5-(4-chlorobenzyl)-5-cyano-2,2-dimethylcyclopentanone (II); said compound is hydrolyzed with acid, preferably strong mineral acid, more preferably sulfuric acid, to provide the desired product 5-(4-chlorobenzyl)-2,2-dimethylcyclopentanone (I).

In order to present a clear understanding of the invention, the following examples are set forth below. These examples are merely illustrative, and are not to be understood as limiting the scope and underlying principles of the invention in any way.

EXAMPLE 1

Preparation of 5-Chloro-2,2-dimethylPentanenitrile

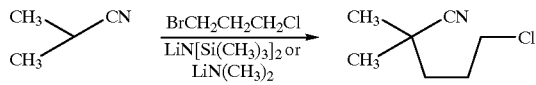

a) Lithium Bis(trimethylsilylamide) Procedure

Isobutyronitrile (13.8 g, 0.20 mole), and 1-bromo-3-chloropropane (34.5 g, 0.22) are added sequentially to a stirred 1 M solution of lithium bis(trimethylsilylamide) (200 ml, 0.20 mole) in hexanes, stirred for two hours at 69° C. and quenched with water. The phases are separated and the organic phase is concentrated in vacuo to afford the title product as an oil, 38.9 g (64% pure, 85.7% yield), identified via gas chromatography.

b) Lithium Dimethylamide Procedure

Isobutyronitrile (9.9 g, 0.143 mole) is added dropwise to a suspension of lithium dimethylamide (7.3 g, 0.143 mole) in hexanes. The resultant anion solution is added to a solution of 1-bromo-3-chloropropane (24.8 g, 0.16 mole) in hexane at 5° to 10° C., warmed to room temperature, and quenched with water. The phases are separated and the organic phase is concentrated in vacuo to afford the title product as a yellow oil, 19.0 g (80% pure, 90.9% yield), identified via gas chromatography.

EXAMPLE 2

Preparation of 2,2-Dimethyladiponitrile

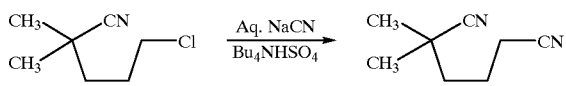

A mixture of 5-chloro-2,2-dimethylpentanenitrile (145.6 g, 1 mole) sodium cyanide (98.0 g, 2 mole), and tetrabutylammonium hydrogen sulfate 10.2 g, 0.03 mole) in water is stirred for 2 hours at 100° C., cooled to room temperature and extracted with ethyl acetate. The extracts are combined, washed with water, and concentrated in vacuo to give a brown oil. The oil is distilled (0.2 torr, 90° C. afford the title product as a colorless oil, 123.7 g (94.9% pure, 91% yield) identified by gas chromatography.

EXAMPLE 3

Preparation of 5-Cyano-2,2-dimethylcyclopentanone

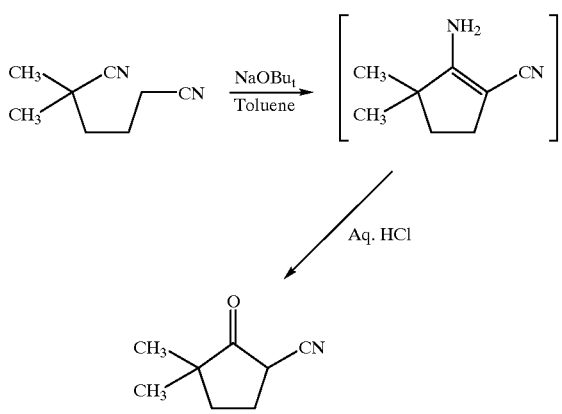

A suspension of potassium t-butoxide (60.2 g, 0.54 mole) in toluene is treated with 2,2-dimethyladiponitrile (120.7 g, 0.87 mole) at 80° C., stirred for 2 hours, cooled to less than 30° C., and quenched with water. The phases are separated, the organic phase is stirred with 3N hydrochloric acid and filtered. The filtrate is concentrated in vacuo to give an oil which is distilled (2 torr, 150° C.) twice to afford the title product as a colorless oil, 65.7 g (98.5% pure, 55% yield), identified by gas chromatography.

EXAMPLE 4

Preparation of 5-(4-chlorobenzyl)-5-cyano-2,2-dimethylcyclopentanone

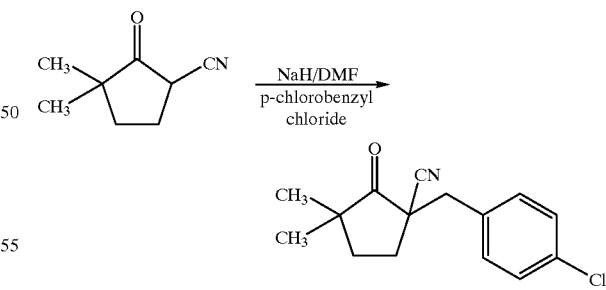

A 60% mineral oil suspension of sodium hydride (12.7 g, 0.31 mole) in dimethylformamide under nitrogen, is treated with cyano-2,2-dimethylcyclopentanone over a 50 minute period at ice-bath temperatures, then with a solution of 4-chloro-benzyl chloride (50.2 g, 0.31 mole) over a 30 minute period, stirred for 5 hours and quenched with water. The resultant mixture is extracted with ethyl acetate. The extracts are combined, washed with water and concentrated in vacuo to afford a solid residue. The residue is titurated with hexane to afford the title product as white crystals, 59.3 g (72.6% yield), mp 101°–103° C., identified by gas chromatography.

EXAMPLE 5

Preparation of 5-(4-chlorobenzyl)-2,2-dimethylcyclopentanone

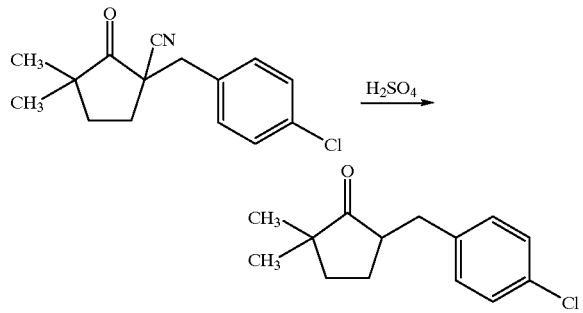

A suspension of 5-(4-chlorobenzyl)-5-cyano-2,2-dimethylcyclopentanone (5.0 g, 0.02 mole) in water is treated with sulfuric acid (50%, 25 ml), stirred for 5 hours at 140° C., cooled to room temperature, and extracted with toluene. The extracts are combined, washed with water, filtered through celite and concentrated in vacuo to afford the title product as a dark oil, 5.5 g (76.5% pure, 93.1% yield), identified by gas chromatography.

What is claimed is:

1. The compound, 5-(4-chlorophenyl)-5-cyano-2,2-dimethylcyclopentanone.

2. A process for the preparation of 5-(4-chlorobenzyl)-2,2-dimethylcyclopentanone which comprises the following steps:

(a) reacting isobutyronitrile with 1-bromo-3-chloropropane in the presence of a first base in a non-polar solvent at a temperature of about 15° C. to 65° C. to afford 5-chloro-2,2-dimethylpentanenitrile;

(b) reacting said 5-chloro-2,2-dimethylpentanenitrile with a cyanide-delivering reagent in the presence of a phase-transfer catalyst to form 2,2-dimethyladiponitrile;

(c) stirring said 2,2-dimethyladiponitrile in the presence of a suspension comprising a second base in a non-polar solvent, and then cooling and quenching to afford 3,3-dimethyl-2-amino-1-cyanocyclopentene;

(d) hydrolyzing said 3,3-dimethyl-2-amino-1-cyanocyclopentene with acid to give 5-cyano-2,2-dimethylcyclopentanone;

(e) reacting said 5-cyano-2,2-dimethylcyclopentanone with 4-chlorobenzyl chloride in the presence of a third base in a polar aprotic solvent to form 5-(4-chlorobenzyl)-5-cyano-2,2-dimethylcyclopentanone; and (f) hydrolyzing said 5-(4-chlorobenzyl)-5-cyano-2,2-dimethylcyclopentanone in the presence of an acid to give the desired 5-(4-chlorobenzyl)-2,2-dimethylcyclopentanone compound.

3. The process according to claim 2 wherein said first base is lithium bis(trimethylsilyl)amide or lithium amide.

4. The process according to claim 2 wherein said non-polar solvent is hexane, heptane, toluene or ethylbenzene.

5. The process according to claim 2 wherein said second base is sodium t-butoxide.

6. The process according to claim 2 wherein said cyanide-delivering reagent is sodium cyanide.

7. The process according to claim 2 wherein said phase-transfer catalyst is tetrabutylammonium hydrogen sulfate.

8. The process according to claim 2 wherein said third base is sodium hydride.

9. The process according to claim 2 wherein said polar aprotic solvent is N,N-dimethylformamide.

10. The process according to claim 2 wherein said acid is sulfuric acid.

11. The process according to claim 4 wherein the first base is lithium bis(trimethylsilyl)amide or lithium amide and the cyanide-delivering agent is sodium cyanide.

12. The process according to claim 11 wherein the second base is sodium t-butoxide and the polar aprotic solvent is N,N-dimethylformamide.

13. The process according to claim 12 wherein the third base is sodium hydride.

14. The process according to claim 13 wherein the acid is sulfuric acid.

* * * * *